United States Patent
Yoshida et al.

(10) Patent No.: US 9,592,028 B2
(45) Date of Patent: Mar. 14, 2017

(54) ULTRASONIC DIAGNOSTIC APPARATUS

(75) Inventors: Tetsuya Yoshida, Nasushiobara (JP);
Tetsuya Kawagishi, Nasushiobara (JP);
Naohisa Kamiyama, Otawara (JP);
Yoko Okamura, Nasushiobara (JP);
Yasuhiko Abe, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 1672 days.

(21) Appl. No.: 12/479,328

(22) Filed: Jun. 5, 2009

(65) Prior Publication Data

US 2009/0306508 A1 Dec. 10, 2009

(30) Foreign Application Priority Data

Jun. 10, 2008 (JP) .................. 2008-151812

(51) Int. Cl.
*A61B 8/00* (2006.01)
*A61B 8/14* (2006.01)
(Continued)

(52) U.S. Cl.
CPC .................. *A61B 8/14* (2013.01); *A61B 8/06* (2013.01); *A61B 8/13* (2013.01); *A61B 8/469* (2013.01); *A61B 8/08* (2013.01); *A61B 8/488* (2013.01)

(58) Field of Classification Search
USPC ................ 345/419, 428; 382/128, 130, 131; 600/407, 437, 438, 439, 441, 443, 447,
(Continued)

(56) References Cited

U.S. PATENT DOCUMENTS 4,790,322 A * 12/1988 Iinuma ..................... 600/456
5,417,219 A * 5/1995 Takamizawa et al. ....... 600/472
(Continued)

FOREIGN PATENT DOCUMENTS

JP 55-103839 8/1980
JP 2000-132664 A 5/2000
(Continued)

OTHER PUBLICATIONS

Office Action issued Jul. 23, 2013, in Japanese Patent Application No. 2009-133187 with English translation.

*Primary Examiner* — Serkan Akar
(74) *Attorney, Agent, or Firm* — Oblon, McClelland, Maier & Neustadt, L.L.P.

(57) ABSTRACT

An ultrasonic diagnostic apparatus disclosed herein comprises an ultrasonic probe which generates an ultrasonic beam, a volume data set collecting unit which collects a plurality of volume data sets corresponding to a plurality of three-dimensional scan ranges via the ultrasonic probe, the plurality of three-dimensional scan ranges partly overlapping one another, a region of interest setting unit which sets, in accordance with a user instruction, a region of interest on a first tomogram generated from particular one of the plurality of volume data sets, a tomogram generating unit which generates the first tomogram from the particular volume data set and also generates a second tomogram associated with a section including the region of interest from another volume data set corresponding to the three-dimensional scan range including the region of interest, and a display unit which displays the first tomogram and the second tomogram.

19 Claims, 6 Drawing Sheets

(51) Int. Cl.
*A61B 8/06* (2006.01)
*A61B 8/13* (2006.01)
*A61B 8/08* (2006.01)

(58) Field of Classification Search
USPC ........ 600/450, 454, 455, 456, 458, 472, 508
See application file for complete search history.

(56) References Cited

U.S. PATENT DOCUMENTS

| | | | |
|---|---|---|---|
| 5,425,365 A * | 6/1995 | Iinuma | 600/455 |
| 5,469,849 A * | 11/1995 | Sasaki et al. | 600/443 |
| 5,509,413 A * | 4/1996 | Akama et al. | 600/438 |
| 5,873,829 A * | 2/1999 | Kamiyama et al. | 600/443 |
| 5,993,391 A * | 11/1999 | Kamiyama | 600/443 |
| 6,149,597 A * | 11/2000 | Kamiyama | 600/458 |
| 6,245,019 B1 * | 6/2001 | Kamiyama | 600/458 |
| 6,436,049 B1 * | 8/2002 | Kamiyama et al. | 600/458 |
| 6,447,453 B1 * | 9/2002 | Roundhill et al. | 600/443 |
| 6,494,834 B2 * | 12/2002 | Konofagou et al. | 600/438 |
| 6,500,118 B1 * | 12/2002 | Hashimoto | 600/437 |
| 6,508,768 B1 * | 1/2003 | Hall et al. | 600/443 |
| 6,540,676 B2 * | 4/2003 | Kamiyama | 600/437 |
| 6,638,225 B2 * | 10/2003 | Kamiyama | 600/443 |
| 6,673,019 B2 * | 1/2004 | Kamiyama | 600/443 |
| 6,773,398 B2 * | 8/2004 | Ogasawara et al. | 600/437 |
| 6,951,543 B2 * | 10/2005 | Roundhill | 600/443 |
| 6,991,606 B2 * | 1/2006 | Kamiyama | 600/458 |
| 7,175,598 B2 * | 2/2007 | Yoneyama | 600/443 |
| 7,239,907 B2 * | 7/2007 | Abe et al. | 600/407 |
| 7,302,850 B2 * | 12/2007 | Kamiyama | 73/606 |
| 7,327,862 B2 * | 2/2008 | Murphy et al. | 382/128 |
| 7,824,337 B2 * | 11/2010 | Abe et al. | 600/441 |
| 7,852,334 B2 * | 12/2010 | Kobayashi | 345/419 |
| 2002/0028994 A1 * | 3/2002 | Kamiyama | 600/437 |
| 2002/0072671 A1 * | 6/2002 | Chenal et al. | 600/450 |
| 2002/0072672 A1 * | 6/2002 | Roundhill et al. | 600/450 |
| 2002/0072674 A1 * | 6/2002 | Criton et al. | 600/454 |
| 2003/0083578 A1 * | 5/2003 | Abe et al. | 600/447 |
| 2003/0135116 A1 * | 7/2003 | Ogasawara et al. | 600/437 |
| 2004/0081340 A1 * | 4/2004 | Hashimoto | 382/128 |
| 2004/0267124 A1 * | 12/2004 | Roundhill | 600/443 |
| 2005/0085729 A1 * | 4/2005 | Abe | 600/450 |
| 2005/0101863 A1 * | 5/2005 | Kawagishi et al. | 600/443 |
| 2005/0119569 A1 * | 6/2005 | Ohtake | 600/437 |
| 2005/0187475 A1 * | 8/2005 | Nakaya | 600/439 |
| 2006/0020205 A1 * | 1/2006 | Kamiyama | 600/437 |
| 2006/0036172 A1 * | 2/2006 | Abe | 600/443 |
| 2006/0084874 A1 * | 4/2006 | Imamura et al. | 600/447 |
| 2006/0098853 A1 * | 5/2006 | Roundhill et al. | 382/128 |
| 2006/0116583 A1 * | 6/2006 | Ogasawara et al. | 600/458 |
| 2006/0122512 A1 * | 6/2006 | Abe | 600/454 |
| 2006/0241447 A1 * | 10/2006 | Harada et al. | 600/443 |
| 2007/0038087 A1 * | 2/2007 | Abe et al. | 600/437 |
| 2007/0118041 A1 * | 5/2007 | Nishiura et al. | 600/508 |
| 2007/0167777 A1 * | 7/2007 | Abe et al. | 600/441 |
| 2007/0239015 A1 * | 10/2007 | Sato | 600/454 |
| 2007/0242069 A1 * | 10/2007 | Matsue et al. | 345/428 |
| 2008/0019580 A1 * | 1/2008 | Ohyu et al. | 382/130 |
| 2008/0051661 A1 * | 2/2008 | Kataguchi et al. | 600/455 |
| 2008/0077013 A1 * | 3/2008 | Kawagishi et al. | 600/443 |
| 2008/0089571 A1 * | 4/2008 | Kurita | 382/131 |
| 2009/0024034 A1 * | 1/2009 | Moreau-Gobard et al. | 600/443 |
| 2009/0306508 A1 * | 12/2009 | Yoshida et al. | 600/443 |
| 2009/0318803 A1 * | 12/2009 | Abe et al. | 600/438 |
| 2010/0041992 A1 * | 2/2010 | Ohuchi et al. | 600/443 |
| 2010/0198072 A1 * | 8/2010 | Abe et al. | 600/443 |

FOREIGN PATENT DOCUMENTS

| | | |
|---|---|---|
| JP | 2001-128975 A | 5/2001 |
| JP | 2003-93382 A | 4/2003 |
| JP | 2004-141514 A | 5/2004 |
| JP | 2006-51360 | 2/2006 |
| JP | 2006-167267 A | 6/2006 |
| JP | 2007-38016 A | 2/2007 |
| JP | 2007-222390 A | 9/2007 |
| JP | 2007-244575 A | 9/2007 |

* cited by examiner

ULTRASONIC DIAGNOSTIC APPARATUS

CROSS-REFERENCE TO RELATED APPLICATIONS

This application is based upon and claims the benefit of priority from prior Japanese Patent Application No. 2008-151812, filed Jun. 10, 2008, the entire contents of which are incorporated herein by reference.

BACKGROUND OF THE INVENTION

1. Field of the Invention

The present invention relates to an ultrasonic diagnostic apparatus capable of three-dimensional (3D) scanning.

2. Description of the Related Art

An ultrasonic diagnostic apparatus enables real-time acquisition of the pulsation of a heart or the motion of a fetus by simple operation of applying an ultrasonic probe to the surface of a body. Moreover, the ultrasonic diagnostic apparatus is free of exposure to radiation unlike X-rays and is thus highly secure and enables repeated examinations, which advantageously allows the use in, for example, obstetrical services or home care services. Further, the ultrasonic diagnostic apparatus is easy to use in that it is smaller in system scale than other diagnostic apparatuses such as X-ray, CT and MRI diagnostic apparatuses and can be easily moved to a bedside for examinations.

On the other hand, in a conventional examination using the ultrasonic diagnostic apparatus, an engineer who uses the ultrasonic probe for scanning changes the way of applying the probe to a region of interest to search for an image that makes the region of interest visible. The image thus obtained is preserved for a doctor to make a diagnosis.

In this case, in order to enable a field of view to be enlarged during the diagnosis by the doctor, a plurality of ultrasonic vibration units are provided to pick up two-dimensional images, and these two-dimensional images are synthesized and then displayed, as disclosed in Jpn. Pat. Appln. KOKAI Publication No. 55-103839.

However, in such a method, the doctor interprets the image within the range of the two-dimensional images of a part which has been scanned by the engineer with suspicion. Therefore, the problem is that when the engineer has overlooked, for example, a tumor during the scanning with the ultrasonic probe, the doctor is unable to detect the tumor.

According to a method that tends to be used in the United States nowadays, the engineer only scans a predetermined region with the ultrasonic probe and preserves images of the region, and the doctor interprets the data and makes a diagnosis. That is to say, the engineer only performs scanning, and the doctor interprets the scanning result and makes a diagnosis. Thus, the engineer is in charge of scanning, and the doctor is in charge of interpretation, so that the two tasks are separated.

On the other hand, there has recently been developed and commercialized an apparatus which performs a so-called three-dimensional scan by applying an ultrasonic beam to a target part so that the target part can be volumetrically observed over time.

The advantage of such a three-dimensional scan capable of collecting volume data sets is that an objective diagnosis can be made. Specifically, as described above, it has heretofore been the case that the doctor makes a diagnosis only using the image of the part which has been scanned by the engineer with suspicion, so that the doctor is unable to detect any new problem in the parts overlooked by the engineer. However, the volume data sets acquired by the engineer by the three-dimensional scanning enables the doctor to reconstruct a given sectional image for observation, such that a diagnosis can be said to be more objective.

Accordingly, it is easily presumed that when the role of the engineer who performs scanning is clearly separated from the role of the doctor who makes a diagnosis as described above, the conventional interpretation with the two-dimensional images may be replaced the interpretation with the volume data sets.

On the other hand, in such a three-dimensional scan, the volume data sets are collected in real time. As a result, the volume of data handled is so great that considerable labor and time are required to reconstruct a given sectional image from the acquired volume data sets to detect a problematic part. Moreover, when the engineer is only allowed to simply perform a scan of the predetermined region as described above, images that can be acquired are limited by the way that the engineer applies the probe at the previous stage. Therefore, even if the doctor finds a part suspected of being affected by a disease as a result of interpreting the images, it is not possible to change the way of applying the probe to acquire an image that clearly shows the characteristics of this part. It is thus difficult to make a high-quality and accurate ultrasonic diagnosis.

BRIEF SUMMARY OF THE INVENTION

It is an object of the present invention to provide an ultrasonic diagnostic apparatus which minimizes reexaminations attributed to unclarity of an image including a part of interest.

According to one aspect of the present invention, there is provided an ultrasonic diagnostic apparatus comprising an ultrasonic probe 12 which generates an ultrasonic beam; a volume data set collecting unit 30b which collects a plurality of volume data sets corresponding to a plurality of three-dimensional scan ranges via the ultrasonic probe, the plurality of three-dimensional scan ranges partly overlapping one another; a region of interest setting unit 251 which sets, in accordance with a user instruction, a region of interest on a first tomogram generated from particular one of the plurality of volume data sets; a tomogram generating unit 252 which generates the first tomogram from the particular volume data set and also generates a second tomogram associated with a section including the region of interest from another volume data set corresponding to the three-dimensional scan range including the region of interest; and a display unit 253 which displays the first tomogram and the second tomogram.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment of the present invention will hereinafter be described with reference to the drawings.

Figure 1:
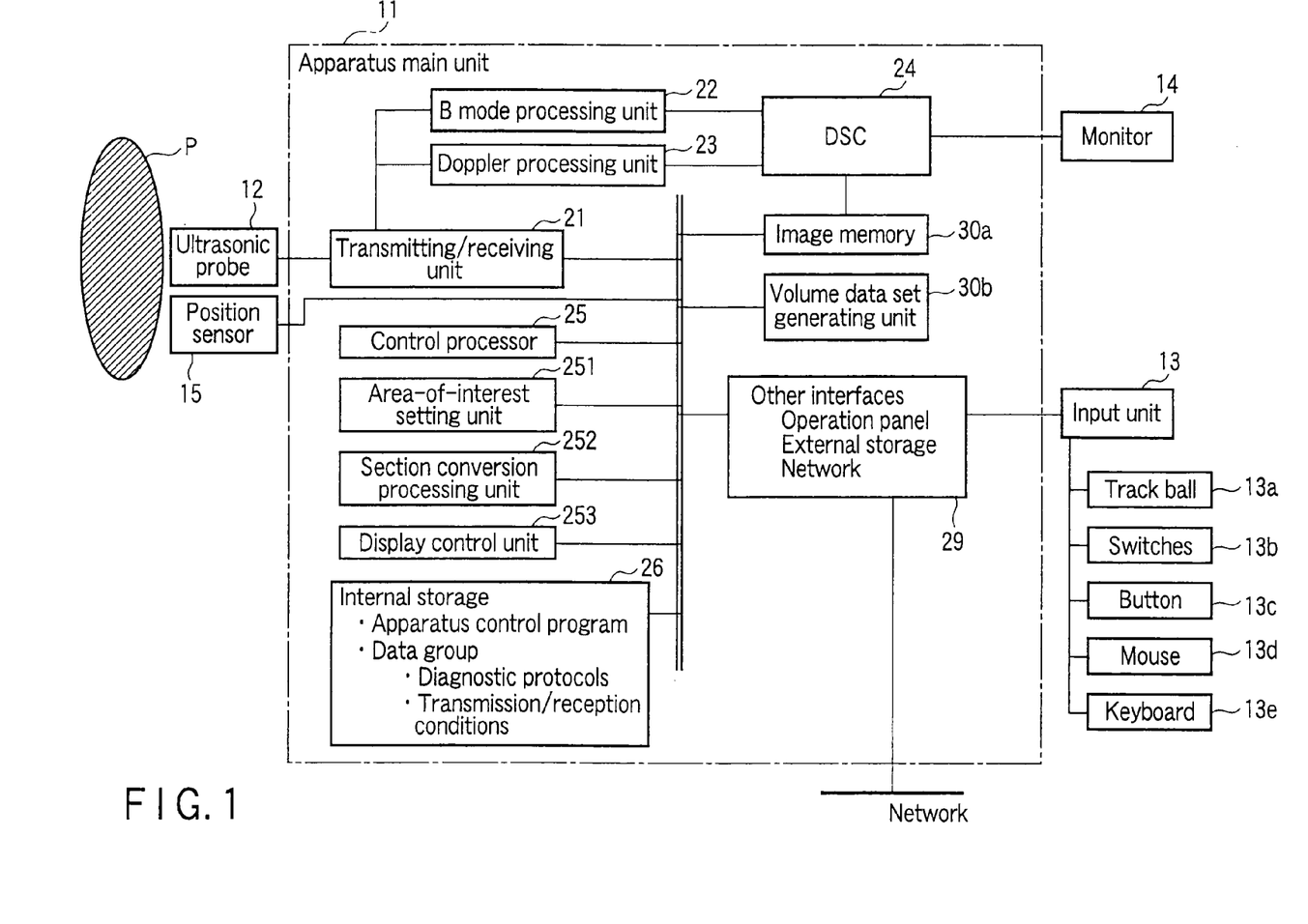
FIG. 1 is a schematic diagram showing the configuration of an ultrasonic diagnostic apparatus according to an embodiment of the present invention.

FIG. 1 shows the configuration of an ultrasonic diagnostic apparatus according to the present embodiment. An apparatus main unit 11 is connected to an ultrasonic probe 12, an input unit 13 and a monitor 14. The ultrasonic probe 12 has a plurality of piezoelectric vibrators. The plurality of piezoelectric vibrators are two-dimensionally arranged to correspond to electronic three-dimensional (3D) scanning. The plurality of piezoelectric vibrators may otherwise be one-dimensionally arranged to correspond to mechanical 3D scanning. The 3D scanning is a single operation for collecting all of a plurality of echo signals in a 3D scan range, and is successively repeated in the 3D scan range at given periods. The 3D scanning includes a plurality of 2D scans. The two-dimensional scanning is a single operation for collecting all of a plurality of echo signals in a 2D scan plane by an ultrasonic beam, and is successively repeated at given periods. The 2D scanning is repeated while the angle of the two-dimensional scan plane is being changed, such that the 3D scanning is completed. In addition, image data generated from the echo signals collected by the 2D scanning is referred to as a 2D data set (SD), while image data generated from the echo signals collected by the 3D scanning is distinctively referred to as a volume data set (VD). Moreover, a position sensor 15 is provided to measure the position of the 3D scanning from the position of the ultrasonic probe 12.

The ultrasonic probe 12 is supplied with a drive signal from an ultrasonic wave transmitting/receiving unit 21. Thus, an ultrasonic beam is generated from the ultrasonic probe 12. Ultrasonic waves are successively reflected by a discontinuous plane of acoustic impedance in a subject P. The ultrasonic probe 12 converts the wave reflected from the subject P into an electric signal, and outputs the electric signal as an echo signal. The amplitude of the echo signal is reflected in the difference of the acoustic impedance. The frequency of the echo signal is shifted from a transmission frequency by a velocity component of the ultrasonic beam in a moving object such as blood or a heart wall.

The input unit 13 has input means such as a track ball 13a, various switches 13b, a button 13c, a mouse 13d, and a keyboard 13e. A user instruction, for example, to select a volume data set and to set a region of interest to a given position on the sectional image generated from the select volume data set is input to the apparatus main unit 11 via the input unit 13. A display control unit 253 generates display screen data including images, etc. The generated display screen data is displayed on the monitor 14 via a digital scan converter 24.

The ultrasonic wave transmitting/receiving unit 21 has, for example, an unshown rate pulse generating circuit, a delay circuit and a pulser circuit. The rate pulse generating circuit generates a rate pulse for forming transmission ultrasonic waves at a predetermined rate frequency frHz (period: 1/fr second). The delay circuit provides the rate pulse for each channel with a delay time necessary to converge the ultrasonic waves into a beam shape and determine transmission directional characteristics. This delay information is changed, so that the direction of transmission from the surface of a probe vibrator can be adjusted to any direction. The pulser circuit generates a drive pulse for each channel synchronously with the rate pulse. The ultrasonic wave transmitting/receiving unit 21 has a function capable of instantaneously changing, for example, the delay information, the transmission frequency and a transmission drive voltage under the instruction of a control processor 25. In particular, the transmission drive voltage is changed by a mechanism which electrically switches a linear amplifier type emitter circuit capable of instantaneously changing its value or a plurality of power units. The ultrasonic wave transmitting/receiving unit 21 also has an unshown amplifier circuit, an A/D converter, an adder, etc. The amplifier circuit amplifies, channel by channel, the echo signals taken in via the ultrasonic probe 12. The A/D converter provides the amplified echo signal with a delay time necessary to determine reception directional characteristics. The adder adds the delayed echo signal. Due to this addition, a reflection component from a direction corresponding to the reception directional characteristics of the echo signal is emphasized, and a synthetic beam for ultrasonic wave transmission/reception is formed by the reception directional characteristics and the transmission directional characteristics.

A B mode processing unit 22 generates B mode image data in which signal intensities are expressed by the strength of luminance, from the echo signal coming from the ultrasonic wave transmitting/receiving unit 21 by logarithmic amplifying processing or envelope detecting processing. The B mode image data is transmitted to the image generating circuit 24, and displayed on the monitor 14 as a B mode image which expresses the strength of a reflected wave by luminance.

A Doppler processing unit 23 performs a frequency analysis of velocity information from the echo signal received from the ultrasonic wave transmitting/receiving unit 21, extracts a Doppler component of the moving object such as blood or a heart attributed to a Doppler effect, and obtains its movement information on, for example, an average velocity, dispersion and power with regard to multiple points. Obtained blood flow information is sent to the digital scan converter 24, and displayed in color on the monitor 14 as an average velocity image, a dispersion image, a power image or a combination of these images.

The digital scan converter 24 converts a scan line signal sequence of ultrasonic scanning into a scan line signal sequence in a general video format typified in, for example, televisions, and generates an ultrasonic diagnostic image as a display image.

An internal storage 26 stores a control program for performing a later-described scan sequence, image generation and display processing, diagnostic information (e.g., patient IDs, doctor's observations), diagnostic protocols, transmission/reception conditions and other data groups. In particular, the internal storage 26 saves the control program for performing the scan sequence for ultrasonic wave transmission/reception. The internal storage 26 is also used to save images in a later-described image memory 30a if necessary. Data in the internal storage 26 can be transferred to external peripheral equipment via an interface circuit 29.

The interface unit 29 is an interface associated with the input unit 13, a network and a new external storage (not shown). Data on an ultrasonic image and the result of an analysis obtained by this apparatus can be transferred by the interface unit 29 to other devices via the network.

The image memory 30a stores a volume data set generated by coordinate conversion and interpolation processing from the 2D data set which has been generated in the B mode processing unit 22 or the Doppler processing unit 23 and from a plurality of 2D data sets in a volume data set generating unit 30b. In addition, the 2D data set and the volume data set are typically, but not exclusively, B mode images representing the morphology of the subject, and may be Doppler images representing moving velocity spatial distribution of the moving object such as blood or a heart.

The control processor 25 has a function as an information processor (calculator), and performs overall control of the apparatus main unit 11 in accordance with the control program.

A region of interest setting unit 251 sets, in accordance with a user instruction, a region of interest on a tomogram (first tomogram) which has been generated by a section conversion processing unit 252 from a particular volume data set selected from a plurality of volume data sets in accordance with a user instruction. The section conversion processing unit 252 generates the first tomogram from the particular volume data set, and also specifies at least another volume data set corresponding to a three-dimensional scan range including the region of interest, and generates a tomogram (second tomogram) associated with a section including the region of interest from the another volume data set.

The display control unit 253 constructs a display screen including the tomogram generated in the section conversion processing unit 252.

Figure 6:
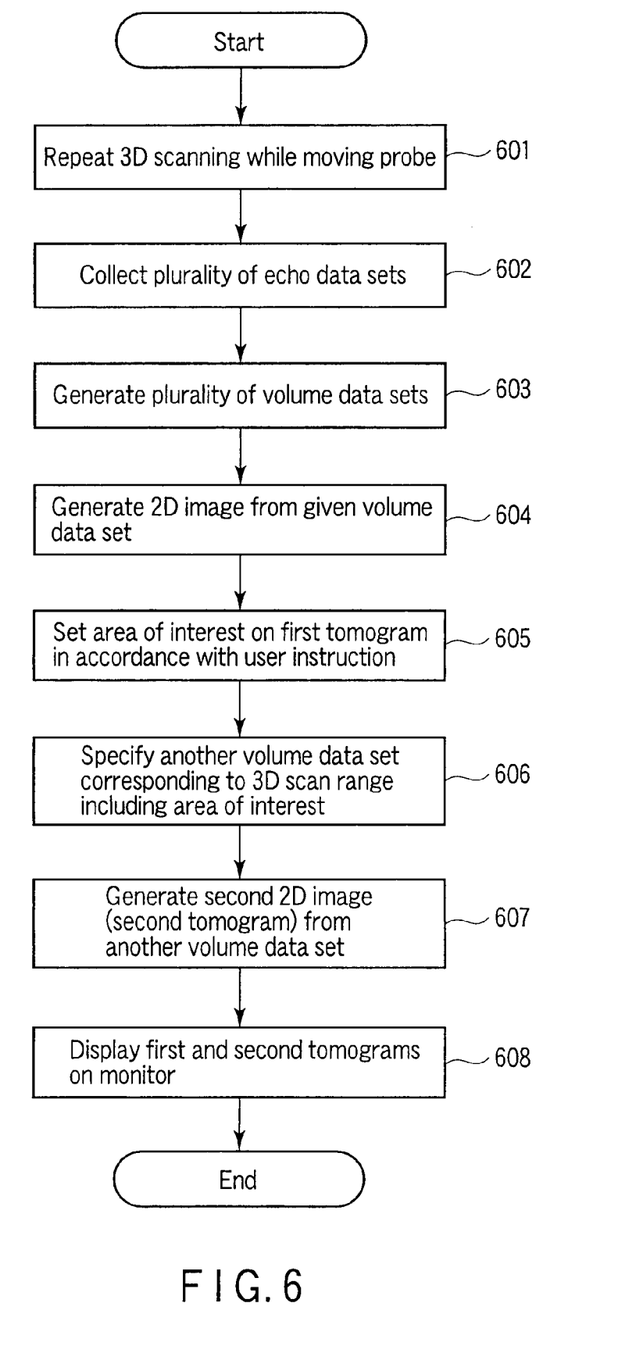
FIG. 6 is a flowchart explaining operation in the present embodiment.

Now, the operation in such a configuration of the embodiment is described in accordance with a flowchart shown in FIG. 6.

The ultrasonic wave transmitting/receiving unit 21 repeats 3D scanning via the ultrasonic probe 12 (step 601).

Figure 2:
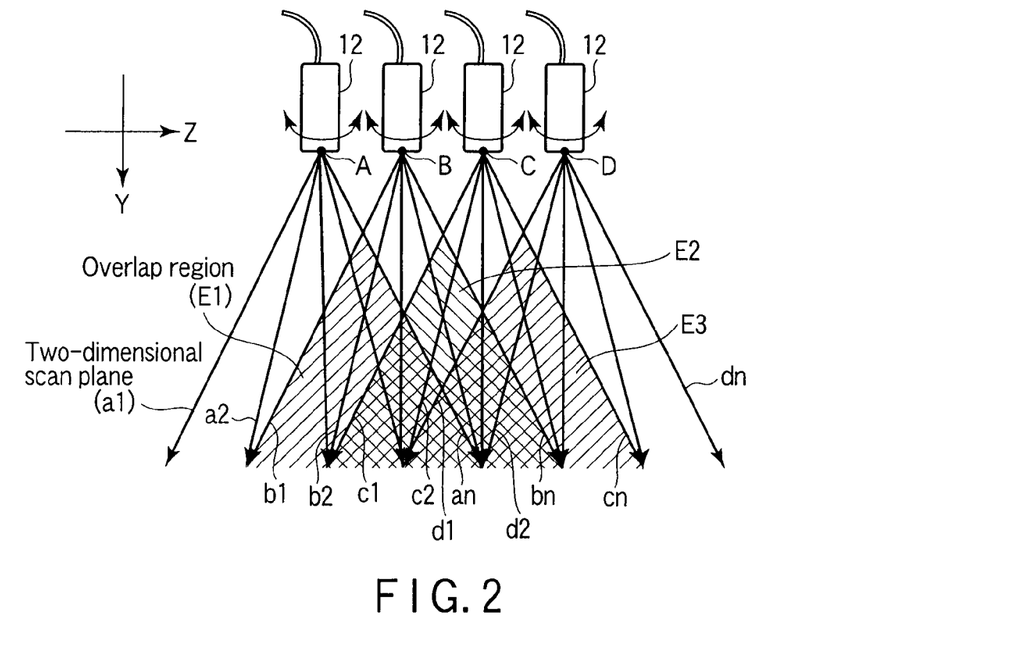
FIG. 2 is a diagram showing an example of data acquired by moving and operating an ultrasonic probe in the present embodiment.
Figure 3:
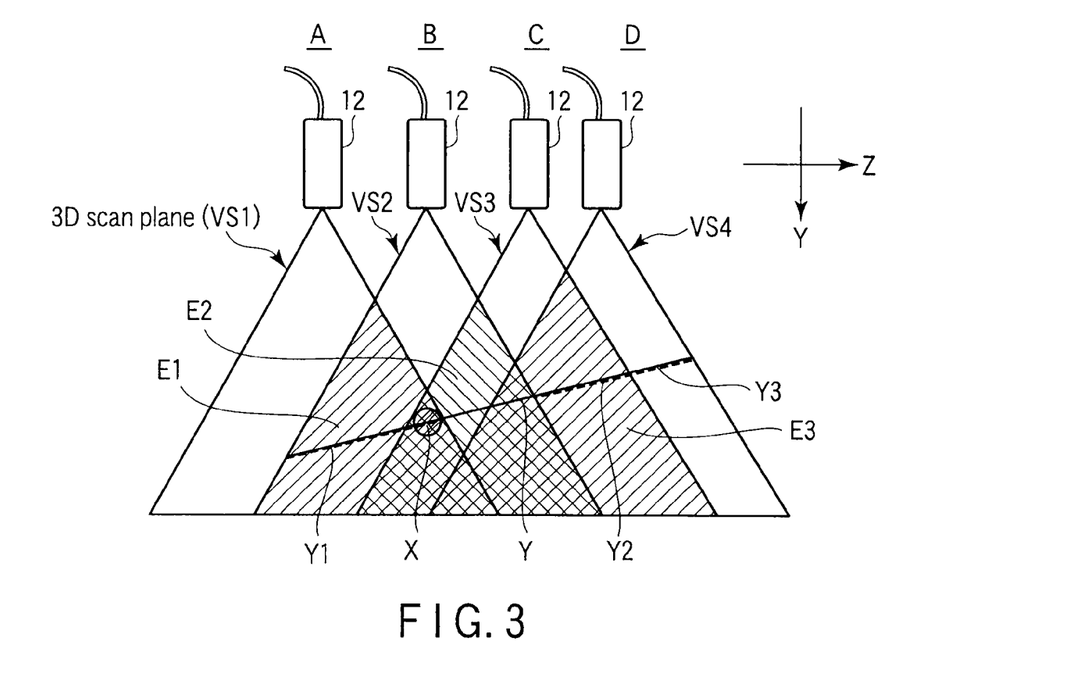
FIG. 3 is a diagram showing an example of the generation of time-series volume data sets in the present embodiment.
Figure 4:
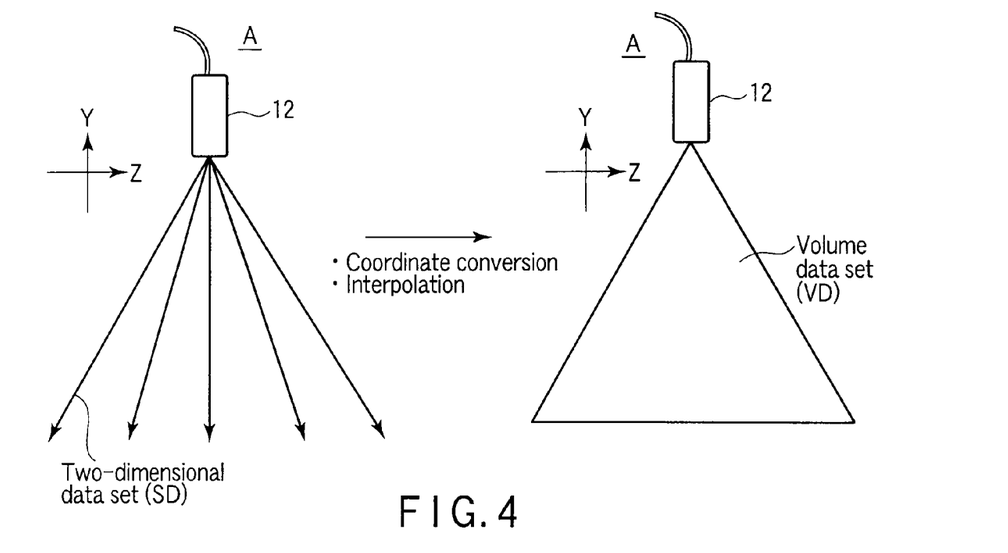
FIG. 4 is a diagram explaining a voxel conversion for generating the time-series volume data set in the present embodiment.
Figure 7:
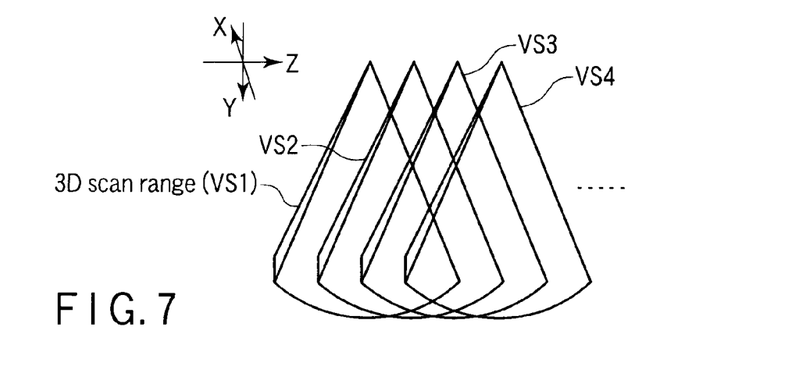
FIG. 7 is a diagram showing a plurality of three-dimensional scan ranges for repeated three-dimensional scanning in the present embodiment.

As shown in FIGS. 2, 3 and 7, an operator moves the ultrasonic probe 12 little by little on the surface of the body of the subject during the repetition of the 3D scanning. The direction of the movement is on a Z-axis. A plurality of echo data sets at different positions A, B, C, D of the ultrasonic probe 12 are collected by the movement (step 602), and a volume data set is generated by the volume data set generating unit 30b as shown in FIG. 4 (step 603).

The position of the 3D scanning is measured by the position sensor 15 for measuring the position of the ultrasonic probe 12. Otherwise, it is possible to use, instead of the position sensor 15, for example, a (auto-)correlation function representing the correlation between the volume data sets, or mutual information for obtaining a difference in distance between data from the position information in the volume data sets.

A plurality of three-dimensional scan ranges VS1, VS2, VS3, VS4 corresponding to the plurality of volume data sets, respectively, partly overlap one another. Here, the three-dimensional scan ranges VS1, VS2 overlap each other in an overlap region E1, the three-dimensional scan ranges VS2, VS3 overlap each other in an overlap region E2, and the three-dimensional scan ranges VS3, VS4 overlap each other in an overlap region E3. Moreover, the three-dimensional scan range VS1 also overlaps the three-dimensional scan ranges VS3, VS4 in addition to the three-dimensional scan range VS2. The three-dimensional scan range VS2 also overlaps the three-dimensional scan range VS4 in addition to the three-dimensional scan ranges VS1, VS3.

Then, an interpreter selects particular one of volume data sets VD1 to VD4, for example, the volume data set VD2 by the input operation of the input unit 13. A tomogram (first tomogram) associated with a predetermined initial section is generated from the selected volume data set VD2 by the section conversion processing unit 252, and displayed on the monitor 14 (step 604). The initial section is a two-dimensional scan plane located, for example, in the center of the three-dimensional scan range VS2. The interpreter shifts the initial section a given distance in a given direction and rotates the section a given angle on a given axis (XYZ) as needed, thereby finally determining a section suitable for a diagnosis. The determined section is indicated by Y in FIG. 3 and indicated by MPR2 in FIG. 8. The tomogram (first tomogram) associated with the determined section is generated from the volume data set VD2 by the section conversion processing unit 252, and displayed on the monitor 14.

Figure 5A:
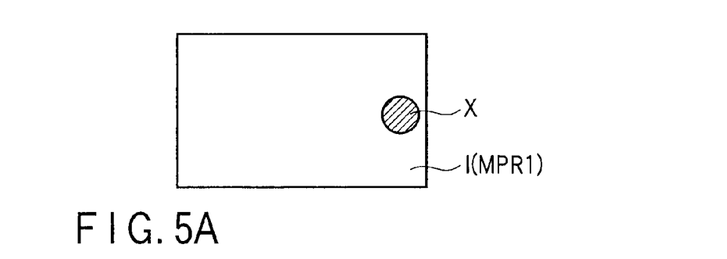
FIG. 5A is a diagram showing an example of display on a monitor in the present embodiment.
Figure 5B:
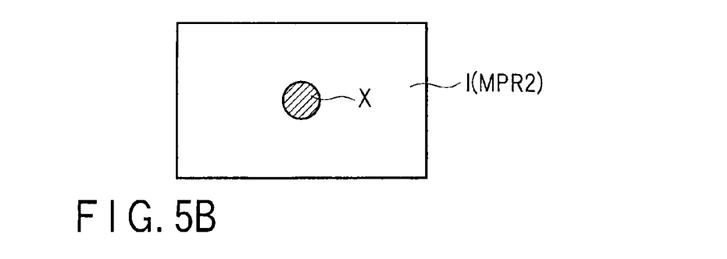
FIG. 5B is a diagram showing an example of display on the monitor in the present embodiment.

The region of interest setting unit 251 sets a region of interest at a designated position on the first tomogram, for example, on a tumor X as shown in FIG. 5B in accordance with the operation of the input unit 13 by the interpreter based on a user instruction (step 605).

Figure 8:
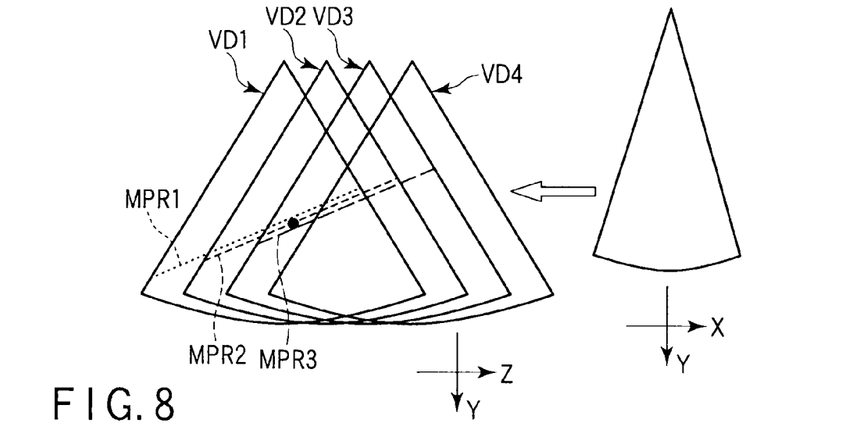
FIG. 8 is a diagram showing sections determined on other volumes with respect to a region of interest and a section that are designated on a particular volume in the present embodiment.

The section conversion processing unit 252 judges whether the region of interest set on the first tomogram is included in the three-dimensional scan ranges VS1, VS3, VS4 of the other volume data sets VD1, VD3, VD4 (step 606). The section conversion processing unit 252 generates tomograms (second tomograms) from the volume data sets VD1, VD3 corresponding to the three-dimensional scan ranges including the region of interest, here, the three-dimensional scan ranges VS1, VS3. As shown in FIG. 8, second tomogram sections MPR1, MPR3 are set to sections which are parallel with and partly overlap a determined section MPR2. The tomograms (second tomograms) associated with the set sections MPR1, MPR3 are respectively generated from the volume data sets VD1, VD3 by the section conversion processing unit 252, and displayed on the monitor 14 (steps 607, 608).

The region of interest is observed on the tomogram (first tomogram) derived from one three-dimensional scanning, while the region of interest can also be observed on the tomogram (second tomogram) derived from the other three-dimensional scanning. Even when the quality of the first tomogram is relatively low and is not suitable for interpretation, this can be compensated for by the second tomogram. Thus, an improvement in the accuracy of interpretation can be expected. Moreover, chances of rescanning can also be reduced.

Furthermore, in the 3D scanning, the volume data sets are collected, and the volume of data handled is therefore great. However, by only setting a region of interest for the volume data sets, a tomogram that provides a multidirectional view of the region of interest can be easily obtained, so that an ultrasonic diagnostic can be efficiently carried out.

As described above, the second tomogram sections MPR1, MPR3 are set to sections which are parallel with and partly overlap the initial section MPR2. However, this is not limitation. A tomogram (original tomogram) of the two-dimensional scan plane has higher spatial resolution and higher quality than the tomogram generated from the volume data set by the section conversion processing. When a particular mode is selected, the first and second tomograms can be limited to the tomograms of the two-dimensional scan plane.

Figure 9:
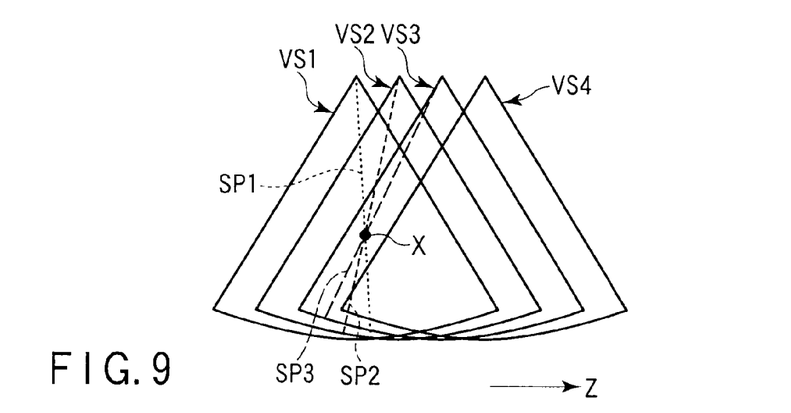
FIG. 9 is a diagram showing sections determined on other volumes with respect to a region of interest and a section that are designated on a particular volume in the present embodiment.

As shown in FIG. 9, a region of interest X is designated on the tomogram (first tomogram) of a two-dimensional scan plane SP2 within the three-dimensional scan range VS2. The section conversion processing unit 252 judges whether the region of interest X set on the first tomogram is included in the three-dimensional scan ranges VS1, VS3, VS4 of the other volume data sets VD1, VD3, VD4. The section conversion processing unit 252 sets two-dimensional scan planes SP1, SP3 which are included in the three-dimensional scan ranges VS1, VS3 and which pass the region of interest X. Tomograms (second tomograms) I(SP1), I(SP3) collected in the set two-dimensional scan planes SP1, SP3 are read from the image memory 30a.

Figure 5C:
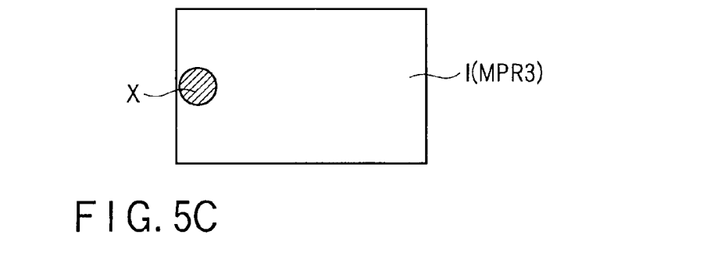
FIG. 5C is a diagram showing an example of display on the monitor in the present embodiment.

Next, the display of the tomograms is described. Tomograms I(MPR1), I(MPR2), I(MPR3) corresponding to the volume data sets VD1, VD2, VD3 are displayed on the monitor 14 (FIG. 5A, FIG. 5B, FIG. 5C). The tomogram I(MPR1) is acquired by scanning with the ultrasonic probe 12 at the position of a point A, and the tumor X located in the overlap region E1 is displayed on the right end of the tomogram I(MPR1). Moreover, the tomogram I(MPR3) is acquired by scanning with the ultrasonic probe 12 at the position of a point C, and the tumor X located in the overlap region E2 is displayed on the left end of the tomogram I(MPR3).

Consequently, the interpreter can simultaneously observe the plurality of tomograms I(MPR1), I(MPR2), I(MPR3) including the same region of interest on the monitor 14 as a result of a plurality of three-dimensional scans.

Figure 10:
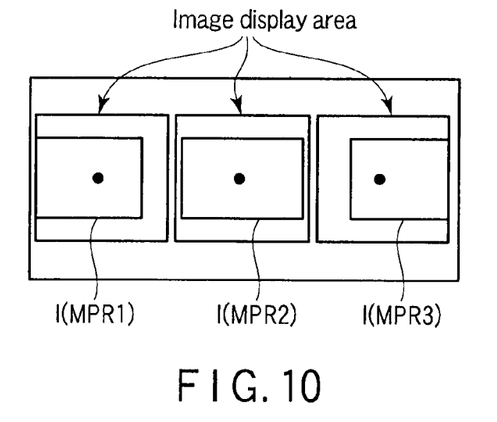
FIG. 10 is a diagram showing an example of image display corresponding to FIG. 8.
Figure 11:
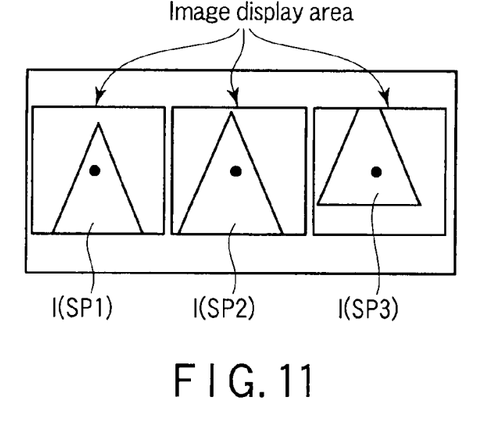
FIG. 11 is a diagram showing an example of image display corresponding to FIG. 9.

As shown in FIG. 10, the display control unit 253 shifts the display positions of the plurality of tomograms I(MPR1), I(MPR2), I(MPR3) including the same region of interest so that the image of the region of interest X may be located in the center of each image display area on the monitor 14. As shown in FIG. 11, in the case where the tomograms I(SP1), I(SP2), I(SP3) collected in the two-dimensional scan planes SP1, SP2, SP3, the display control unit 253 also shifts the display positions of the tomograms I(SP1), I(SP2), I(SP3) so that the image of the region of interest X may be located in the center of each image display area on the monitor 14.

As the region of interest X is always located in the center of each display area, the interpreter does not have to search for the region of interest X, thereby allowing the interpretation work to be efficient.

Although the tomograms of all the volume data sets acquired for the points A to D are used in the example described above, the volume data sets can be thinned out and used. For example, a volume data set acquired every moving distance is used, and the positions of the tumor in the tomograms of these volume data sets can be displayed in association with one other.

(Modification)

In the embodiment described above, a strait line Y is set as a region of interest in a two-dimensional tomogram of a volume data set, and a tomogram sliced off along the strait line Y is displayed on the monitor 14. However, for example, a cubic region of interest such as a spherical region of interest including a part of interest may be set in a three-dimensional (3D) image of the volume data set, and a corresponding 3D image may be generated from each volume data set on the basis of the region of interest and displayed on the monitor 14.

Figure 12:
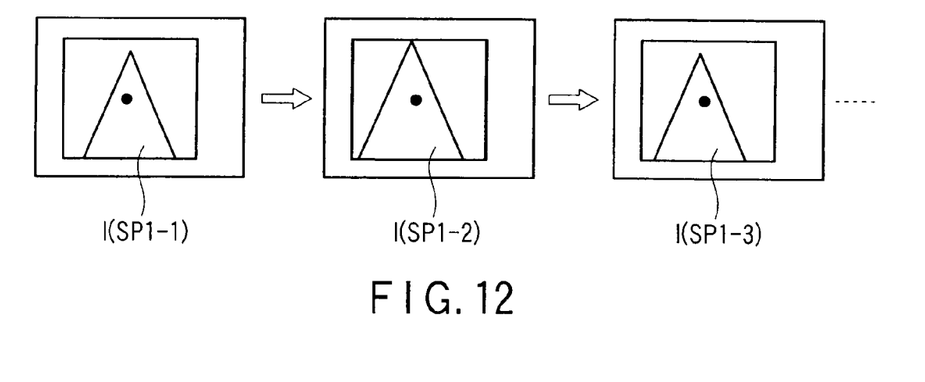
FIG. 12 is a diagram showing an example of image display according to a modification of the present embodiment.

The idea of the present embodiment generates the following application. When three-dimensional scanning is repeated at the same position, a plurality of volume data sets associated with the same three-dimensional scan range are generated. A tomogram associated with a given section including a region of interest is generated from a particular volume data set and displayed. A plurality of tomograms at different scanning times associated with the same section are generated. As shown in FIG. 12, tomograms I(SP1-1), I(SP1-2), I(SP1-3) are shifted so that the image of the region of interest in each tomogram may be located in the center of each image display area on the monitor 14.

Furthermore, the present invention is not limited to the embodiment described above, and various modifications can be made without departing from the spirit thereof at the stage of carrying out the invention. For example, a plurality of tomograms A2 to D2 are displayed on the monitor 14 in the embodiment described above. Otherwise, one of the tomograms alone may be displayed on the monitor 14 so that the display is sequentially switched to the other tomograms, for example, by operating the track ball 13a of the input unit 13. Moreover, in the embodiment described above, a region of interest is set so that a tomogram including the region of interest is generated from the volume data sets and displayed. However, a tomogram including the region of interest may be selected from time-series volume data sets acquired at the points A to D before a voxel conversion and displayed. Thus, since the time-series volume data sets before the voxel conversion have greater volumes of data than the volume data sets after the voxel conversion, such time-series volume data sets can be used to generate an image having high resolution.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnostic apparatus, comprising:
   an ultrasonic probe configured to generate an ultrasonic beam;
   a volume data set collector configured to collect a plurality of volume data sets corresponding to a plurality of three-dimensional scan ranges via the ultrasonic probe, the plurality of three-dimensional scan ranges partly overlapping one another;
   a region of interest setting device configured to set, in accordance with a user instruction, a region of interest on a first tomogram generated from a particular one of the plurality of volume data sets, the region of interest being set within a scan range of the plurality of three-dimensional scan ranges that corresponds to the particular one of the plurality of volume data sets;
   a tomogram generator configured to generate the first tomogram from the particular one of the volume data sets and also generate a second tomogram associated with a section including the region of interest from another volume data set of the plurality of volume data sets that has a corresponding three-dimensional scan range that includes the region of interest, wherein the tomogram generator specifies a position of the second tomogram in the another volume data set; and
   a display configured to display the first tomogram and the second tomogram.

2. The ultrasonic diagnostic apparatus according to claim 1, wherein the tomogram generator is configured to generate the first and second tomograms so that a section of the second tomogram partly overlaps a section of the first tomogram.

3. The ultrasonic diagnostic apparatus according to claim 1, wherein the tomogram generator is configured to generate the first and second tomograms so that sections of the first and second tomograms are two-dimensional scan planes formed by the ultrasonic beam.

4. The ultrasonic diagnostic apparatus according to claim 1, wherein the tomogram generator is configured to generate the first and second tomograms so that a section of the second tomogram intersects with a section of the first tomogram.

5. The ultrasonic diagnostic apparatus according to claim 1, further comprising a display controller configured to display the first tomogram in a first display region of the display and to display the second tomogram in a second display region of the display, wherein a position of the region of interest displayed within the second display region is the same as a position of the region of interest displayed within the first display region.

6. The ultrasonic diagnostic apparatus according to claim 1, further comprising an operation interface operated by a user to designate a location of the region of interest on the first tomogram.

7. The ultrasonic diagnostic apparatus according to claim 1, further comprising a display controller configured to display the first tomogram and the second tomogram simultaneously or in a switched manner.

8. The ultrasonic diagnostic apparatus according to claim 1, further comprising a display controller configured to display the first tomogram and the second tomogram in an overlapping manner so that the region of interests in the first and second tomograms are in alignment.

9. The ultrasonic diagnostic apparatus according to claim 1, further comprising a synthesizer configured to generate one synthetic image including an average luminance or maximum luminance from the first tomogram and the second tomogram.

10. The ultrasonic diagnostic apparatus according to claim 1, wherein the tomogram generator is configured to designate the another volume data set corresponding to the three-dimensional scan range that includes the region of interest.

11. An ultrasonic diagnostic apparatus, comprising:
    an ultrasonic probe which generates an ultrasonic beam;
    a volume data set collector configured to scan a three-dimensional scan range to collect a plurality of volume data sets via the ultrasonic probe;
    a region of interest setting device configured to set, in accordance with a user instruction, a region of interest on a first tomogram generated from a particular one of the plurality of volume data sets, the region of interest being set within the three-dimensional scan range;
    a tomogram generator configured to generate the first tomogram from the particular one of the volume data sets and also generate a second tomogram associated with a section including the region of interest from another volume data set of the plurality of volume data sets that includes the region of interest, wherein the tomogram generator specifies a position of the second tomogram in the another volume data set; and
    a display configured to display the first tomogram and the second tomogram.

12. The ultrasonic diagnostic apparatus according to claim 11, wherein the tomogram generator is configured to generate the first and second tomograms so that a section of the second tomogram is the same as a section of the first tomogram.

13. The ultrasonic diagnostic apparatus according to claim 11, wherein the tomogram generator is configured to generate the first and second tomograms so that a section of the second tomogram is a two-dimensional scan plane formed by the ultrasonic beam.

14. The ultrasonic diagnostic apparatus according to claim 11, wherein the tomogram generator is configured to generate the first and second tomograms so that a section of the second tomogram intersects with a section of the first tomogram.

15. The ultrasonic diagnostic apparatus according to claim 11, further comprising a display controller configured to display the first tomogram in a first display region of the display and to display the second tomogram in a second display region of the display, wherein a position of the region of interest displayed within the second display region is the same as a position of the region of interest displayed within the first display region.

16. The ultrasonic diagnostic apparatus according to claim 11, further comprising an operation interface operated by a user to designate a location of the region of interest on the first tomogram.

17. The ultrasonic diagnostic apparatus according to claim 11, further comprising a display controller configured to display the first tomogram and the second tomogram simultaneously or in a switched manner.

18. The ultrasonic diagnostic apparatus according to claim 11, further comprising a display controller configured to display the first tomogram and the second tomogram in an overlapping manner so that the region of interests in the first and second tomograms are in alignment.

19. The ultrasonic diagnostic apparatus according to claim 11, further comprising a synthesizer configured to generate one synthetic image including an average luminance or maximum luminance from the first tomogram and the second tomogram.

* * * * *